(12) United States Patent
Dyckman et al.

(10) Patent No.: US 7,253,170 B2
(45) Date of Patent: Aug. 7, 2007

(54) PYRAZOLE-AMINE COMPOUNDS USEFUL AS KINASE INHIBITORS

(75) Inventors: Alaric J. Dyckman, Lawrenceville, NJ (US); Jagabandhu Das, Mercerville, NJ (US); Katerina Leftheris, Skillman, NJ (US); Chunjian Liu, Pennington, NJ (US); Robert V. Moquin, East Brunswick, NJ (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/477,010

(22) Filed: Jun. 28, 2006

(65) Prior Publication Data

US 2006/0247247 A1    Nov. 2, 2006

Related U.S. Application Data

(62) Division of application No. 10/838,006, filed on May 3, 2004, now Pat. No. 7,151,113.

(60) Provisional application No. 60/467,029, filed on May 1, 2003.

(51) Int. Cl.
| | |
|---|---|
| *A61K 31/501* | (2006.01) |
| *A61K 31/4709* | (2006.01) |
| *A61K 31/454* | (2006.01) |
| *A61K 31/4439* | (2006.01) |
| *A61K 31/4152* | (2006.01) |
| *C07D 403/02* | (2006.01) |

(52) U.S. Cl. ............... 514/252.05; 514/314; 514/326; 514/341; 514/367; 544/238; 546/167; 546/211; 546/275.4; 548/375.1

(58) Field of Classification Search ............... 514/314, 514/326, 341; 544/238; 546/167, 211; 548/375.1
See application file for complete search history.

(56) References Cited

U.S. PATENT DOCUMENTS

| | | | |
|---|---|---|---|
| 4,200,750 | A | 4/1980 | Warner, Jr. et al. |
| 5,712,279 | A | 1/1998 | Biller et al. |
| 5,739,135 | A | 4/1998 | Biller et al. |
| 5,760,246 | A | 6/1998 | Biller et al. |
| 6,184,231 | B1 | 2/2001 | Hewawasam et al. |
| 6,548,529 | B1 | 4/2003 | Robl et al. |
| 6,706,711 | B2 | 3/2004 | Hale |
| 6,706,720 | B2 | 3/2004 | Atwal et al. |
| 2002/0065270 | A1 | 5/2002 | Moriarty et al. |
| 2002/0137747 | A1 | 9/2002 | Moriarty et al. |
| 2003/0139435 | A1 | 7/2003 | Ahmed et al. |
| 2004/0039033 | A1 | 2/2004 | Atwal et al. |

FOREIGN PATENT DOCUMENTS

WO    WO 02/062804    8/2002

WO    WO02/096905    12/2002
WO    WO 2003037274 A2 *  5/2003

OTHER PUBLICATIONS

Ahn, H.-S. et al., "Potent Tetracyclic Guanine Inhibitors of PDE1 and PDE5 Cyclic Guanosine Monophosphate Phosphodiesterases with Oral Antihypertensive Activity", J. Med. Chem., vol. 40, No. 14, pp. 2196-2210 (1997).
Greene, T.W. et al., Protective Groups in Organic Synthesis, Third Editon, John Wiley & Sons, Inc., publ., pp. xi-xii (table of contents) (1999).
Henry, J.R. et al., "p38 mitogen-activated protein kinase as a target for drug discovery", Drugs of the Future, vol. 24, No. 12, pp. 1345-1354 (1999).
Manning, G. et al., "The Protein Kinase Complement of the Human Genome", Science, vol. 298, pp. 1912-1916, 1933-1934 (2002).
Moreland, L.W. et al., "Etanercept Therapy in Rheumatoid Arthritis: A Randomized, Controlled Trial", Ann. Intern. Med., vol. 130, No. 6, pp. 478-486 (1999).
Raingeaud, J. et al., "MKK3- and MKK6-Regulated Gene Expression Is Mediated by the p3B Mitogen-Activated Protein Kinase Signal Transduction Pathway", Molecular and Cellular Biology, vol. 16, No. 3, pp. 1247-1255 (1996).
Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).
Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).
Klunge et al., "Radical Reactions of N-Heterocyclic Compounds, XV[1]", Monatschefte fuer Chemie (1997), 128 (3) 261-270.

* cited by examiner

*Primary Examiner*—Kamal A. Saeed
(74) *Attorney, Agent, or Firm*—Maureen P. O'Brien

(57) ABSTRACT

The present invention provides pyrazole derived compounds of formula (I)

(I)

useful for treating p38 kinase-associated conditions, where W, X, $R_1$, $R_2$, $R_3$, $R_4$, $R_5$, $R_6$ and m are as defined herein. The invention further pertains to pharmaceutical compositions containing at least one compound according to the invention useful for treating p38 kinase-associated conditions, and methods of inhibiting the activity of p38 kinase in a mammal.

10 Claims, No Drawings

PYRAZOLE-AMINE COMPOUNDS USEFUL AS KINASE INHIBITORS

CROSS-REFERENCE TO RELATED APPLICATIONS

This Application is a divisional of U.S. application Ser. No. 10/838,006, filed May 3, 2004, now U.S. Pat. No. 7,151,113 which in turn claims benefit under 35 U.S.C. § 119 of U.S. application Ser. No. 60/467,029, filed May 1, 2003, the entire contents of which are incorporated herein by reference.

FIELD OF THE INVENTION

This invention relates to pyrazole derived compounds useful for treating p38 kinase-associated conditions. The invention further pertains to pharmaceutical compositions containing at least one compound according to the invention useful for treating p38 kinase-associated conditions, and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, Vol. 24 (1999), at pp. 1345-54; Salituro et al., *Curr. Med. Chem.*, Vol. 6 (1999), at pp. 807-823]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, Vol. 34 (1995), at pp. 334-42], and soluble TNF-α receptor-Fc fusion protein (Etanercept) [Moreland et al., *Ann. Intern. Med.*, Vol. 130 (1999), at pp. 478-86].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has established the effectiveness of p38 inhibitors in treating those diseases. The present invention provides pyrazole derived compounds, useful as kinase inhibitors, in particular, as inhibitors of p38 kinase.

SUMMARY OF THE INVENTION

The present invention pertains to compounds having the formula (I), or a pharmaceutically acceptable salt or solvate thereof, which compounds are useful as kinase inhibitors, in particular, p38 kinase inhibitors:

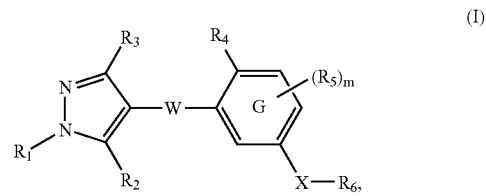

(I)

wherein the symbols have the following meanings unless otherwise indicated, and are, for each occurrence, independently selected:

ring G is phenyl or pyridyl;

W is —NH(C=O)(CHR$_8$)$_r$—, —CH(R$_8$)NH—, —NHCH(R$_8$)—, —CH$_2$—O—, or —(C=O)O—, wherein R$_8$ is hydrogen or alkyl, and r is 0, 1 or 2;

R$_1$ is hydrogen, alkyl, substituted alkyl, aryl, substituted aryl, heteroaryl, substituted heteroaryl, cycloalkyl, substituted cycloalkyl, heterocyclo or substituted heterocyclo, or —(C=O)R$_{18}$;

R$_2$ is hydrogen, alkyl, substituted alkyl, alkoxy, substituted alkoxy, amino, alkylamino, substituted alkylamino, cycloamino, or substituted cycloamino;

R$_3$ is hydrogen, trifluoromethyl, trifluoromethoxy, halogen, cyano, nitro, C$_{1-4}$alkyl, substituted C$_{1-4}$alkyl, NR$_{11}$R$_{12}$, or OR$_{11}$;

R$_4$ is hydrogen, C$_{1-4}$alkyl, substituted C$_{1-4}$alkyl, halogen, trifluoromethyl, trifluoromethoxy, cyano, nitro, or OR$_{13}$;

R$_5$ is at each occurrence independently selected from trifluoromethyl, trifluoromethoxy, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, heteroaryl or substituted heteroaryl, OR$_{13}$, SR$_{13}$, S(=O)R$_{14}$, S(=O)$_2$R$_{14}$, P(=O)$_2$R$_{14}$, S(=O)$_2$OR$_{15}$, P(=O)$_2$OR$_{14}$, NR$_{13}$R$_{14}$, NR$_{13}$S(=O)$_2$R$_{15}$, NR$_{13}$P(=O)$_2$R$_{14}$, S(=O)$_2$NR$_{13}$R$_{14}$, P(=O)$_2$NR$_{13}$R$_{14}$, C(=O)OR$_{13}$, C(=O)R$_{13}$, C(=O)NR$_{13}$R$_{14}$, OC(=O)R$_{13}$, OC(=O)NR$_{13}$R$_{14}$, NR$_{13}$C(=O)OR$_{14}$, NR$_{16}$C(=O)NR$_{13}$R$_{14}$, NR$_{16}$S(=O)$_2$NR$_{13}$R$_{14}$, NR$_{16}$P(=O)$_2$NR$_{13}$R$_{14}$, NR$_{13}$C(=O)R$_{14}$, and/or NR$_{13}$P(=O)$_2$R$_{14}$;

X is —(C=O)NH—, —NH(C=O)—, —NH(C=O)O—, —SO$_2$NH—, —CO$_2$—, or is absent;

R$_6$ is hydrogen, alkyl or substituted alkyl, alkoxy or substituted alkoxy, phenoxy or substituted phenoxy, cycloalkyl or substituted cycloalkyl, heterocycle or substituted heterocycle, aryl or substituted aryl, heteroaryl or substituted heteroaryl; or where X is absent, R$_6$ can be halogen, cyano, trifluoromethyl, alkyl, amino, or alkylamino; or alternatively, R$_6$ is joined together with a group R$_5$ on an adjacent carbon atom to form an optionally-substituted, fused five to six membered heterocyclic or carbocyclic ring;

R$_{11}$, R$_{12}$, R$_{13}$, R$_{14}$, R$_{15}$, R$_{16}$ and R$_{17}$ are independently at each occurrence selected from hydrogen, alkyl, substituted alkyl, cycloalkyl or substituted cycloalkyl, heterocycle or substituted heterocycle, aryl or substituted aryl, and heteroaryl or substituted heteroaryl, except R$_{15}$ is not hydrogen;

$R_{18}$ is hydrogen, alkyl or substituted alkyl, alkenyl or substituted alkenyl, alkynyl or substituted alkynyl, cycloalkyl or substituted cycloalkyl, heterocycle or substituted heterocycle, heteroaryl, or substituted heteroaryl, aryl or substituted aryl; and m is 0, 1, 2 or 3; or a pharmaceutically-acceptable salt, hydrate, solvent, isomer, or prodrug thereof.

FURTHER DESCRIPTION OF THE INVENTION

Further aspects of the invention will be apparent to one skilled in the field upon reading the disclosure herein.

Definitions

The following are definitions of terms used in the present specification and claims. The initial definition provided for a group or term herein applies to that group or term throughout the present specification and claims herein individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, 1-methylpropyl, n-butyl, t-butyl, isobutyl, pentyl, hexyl, isohexyl, heptyl, dimethylpentyl, diethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. A lower alkyl is a "$C_1$-$C_4$ alkyl." When alkyl, lower alkyl (or $C_1$-$C_4$alkyl) is used as a suffix following another named group, such as "hydroxyalkyl" or hydroxyl(lower alkyl), this is intended to refer to an alkyl or lower alkyl ($C_1$-$C_4$alkyl) having bonded thereto one, two or three of the other, specifically-named group(s) at any point of attachment on either the straight or branched chain of the alkyl. As a further example, arylalkyl includes groups such as benzyl or phenylethyl. When the term "substituted" is used with such groups, as in "substituted arylalkyl" or "substituted alkoxyalkyl," it should be understood that either the alkyl moiety, the other named moiety, or both, may be substituted with groups selected from those recited herein as appropriate, e.g., for the alkyl moiety, groups may be selected from those recited below for substituted alkyl, and for the other, specifically-named group, groups may be selected from those recited below for that group.

"Substituted alkyl" refers to an alkyl group as defined above substituted with one or more substituents, preferably 1 to 4 substituents, more preferably 1 to 2 substitutents, at any available point of attachment on the straight and/or branched chain. Exemplary substituents may include but are not limited to one or more of halogen, haloalkyl (e.g., a single halo substituent or multiple halo substitutents forming, in the latter case, groups such as a perfluoroalkyl group including for example, —$CHCl_2$ and/or $CF_3$), haloalkoxyl (e.g., including trifluoromethoxy), cyano, nitro, alkenyl, alkynyl, cycloalkyl, heterocycle, heteroaryl, aryl, $OR_a$, $SR_a$, $S(=O)R_e$, $S(=O)_2R_e$, $P(=O)_2R_e$, $S(=O)_2OR_e$, $P(=O)_2OR_e$, $P(=O)(OR)_2$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $C(=O)ONR_bR_c$, $OC(=O)NR_bR_c$, $NR_bC(=O)OR_a$, $NR_dC(=O)NR_bR_c$, $NR_dS(=O)_2NR_bR_c$, $NR_dP(=O)_2NR_bR_c$, $NR_bC(=O)R_a$, and/or $NR^bP(=O)_2R_e$, wherein $R_a$, $R_b$, $R_c$, $R_d$ and $R_e$ are selected from hydrogen, alkyl, alkenyl, aminoalkyl, alkylaminoalkyl, cycloalkyl(alkyl), aryl(alkyl), heterocyclo(alkyl), heteroaryl(alkyl), cycloalkyl, aryl, heterocyclo, and/or heteroaryl, except $R_e$ is not hydrogen; and additionally, when $R_b$ and $R_c$ are attached to the same nitrogen atom, they may be joined together to form a cycloamino group. Each of $R_a$, $R_b$, $R_c$, $R_d$ and/or $R_e$ on the alkyl and/or cyclic moieties in turn may be optionally substituted with one to three groups, preferably substituted with up to two groups (0 to 2 groups), selected from lower alkyl, lower alkenyl, $R_f$, and a lower alkyl or lower alkenyl substituted with one to two $R_f$, wherein $R_f$ is selected from one or more of cyano, halogen, halo$C_1$-$C_4$alkyl, halo$C_1$-$C_4$alkoxy, keto (=O) (where valence allows), nitro, OH, O($C_1$-$C_4$alkyl), SH, S($C_1$-$C_4$alkyl), S(=O)($C_1$-$C_4$alkyl), S(=O)$_2$($C_1$-$C_4$alkyl), $NH_2$, NH($C_1$-$C_4$alkyl), N($C_1$-$C_4$alkyl)$_2$, NH(cycloalkyl), NH(phenyl), phenyl, benzyl, phenoxy, benzyloxy, NHS(=O)$_2$(alkyl), S(=O)$_2NH_2$, S(=O)$_2$NH($C_1$-$C_4$alkyl), S(=O)$_2$N($C_1$-$C_4$alkyl)$_2$, S(=O)$_2$NH(cycloalkyl), S(=O)$_2$NH(phenyl), C(=O)OH, C(=O)O($C_1$-$C_4$alkyl), C(=O)H, C(=O)($C_1$-$C_4$alkyl), C(=O)$NH_2$, C(=O)NH($C_1$-$C_4$alkyl), C(=O)N($C_1$-$C_4$alkyl)$_2$, C(=O)NH(cycloalkyl), C(=O)NH(phenyl), C(=O)$ONH_2$, C(=O)ONH($C_1$-$C_4$alkyl), C(=O)ON($C_1$-$C_4$alkyl)$_2$, C(=O)ONH(cycloalkyl), C(=O)ONH(phenyl), NHC(=O)O$C_1$-$C_4$alkyl, N($C_1$-$C_4$alkyl)C(=O)O($C_1$-$C_4$alkyl), NHC(=O)$NH_2$, NHC(=O)NH($C_1$-$C_4$alkyl), NHC(=O)N($C_1$-$C_4$alkyl)$_2$, NHC(=O)NH(cycloalkyl), NHC(=O)NH(phenyl), NHC(=O)H, and/or NHC(=O)($C_1$-$C_4$alkyl).

The term "alkenyl" refers to a straight or branched chain hydrocarbon radical containing from 2 to 12 carbon atoms and at least one carbon-carbon double bond. Exemplary such groups include ethenyl and allyl. Lower alkenyl means an alkenyl group of 2 to 4 carbon atoms. "Substituted alkenyl" refers to an alkenyl group substituted with one or more substituents, preferably 1 to 4 substituents, more preferably 1 to 2 substituents, at any available point of attachment. Exemplary substituents may include, but are not limited to, alkyl, substituted alkyl, and those groups recited above as exemplary substituents for substituted alkyl groups.

The term "alkynyl" refers to a straight or branched chain hydrocarbon radical containing from 2 to 12 carbon atoms and at least one carbon-to-carbon triple bond. Exemplary such groups include ethynyl. "Substituted alkynyl" refers to an alkynyl group substituted with one or more substituents, preferably 1 to 4 substituents, more preferably 1 to 2 substituents, at any available point of attachment. Exemplary substituents include, but are not limited to, alkyl, substituted alkyl, and those groups recited above as exemplary substituents for substituted alkyl groups.

The term "alkoxy" refers to the group $OR_g$, wherein $R_g$ is selected from alkyl, alkenyl, or cycloalkyl. A $C_1$-$C_4$alkoxy is an alkoxy group $OR_{g'}$ wherein $R_{g'}$ is a $C_1$-$C_4$alkyl or $C_3$-$C_4$cycloalkyl. A substituted alkoxy group is an alkoxy group as defined above wherein at least one of the alkyl, alkenyl, and/or cycloalkyl moieties is substituted with one or more, preferably 1 to 4, more preferably 1 to 2, groups selected from those recited above for substituted alkenyl groups.

The term "amino" refers to $NH_2$, and an alkylamino refers to an amino group wherein one or both of the hydrogen atoms is or are replaced with a group chosen from alkyl, alkenyl, and/or cycloalkyl. Thus, alkylamino refers to the group $NR_hR_i$, wherein $R_h$ and $R_i$ are selected from hydrogen, alkyl, alkenyl, and/or cycloalkyl, provided $R_h$ and $R_i$ are not both hydrogen. "Aminoalkyl" refers to an alkyl group as defined above substituted with an amino group, and an "alkylaminoalkyl" refers to an alkyl group as defined above substituted with one or more alkylamino groups. A substituted alkylamino group is an alkylamino group wherein at least one of the alkyl, alkenyl, and/or cycloalkyl moieties is substituted with one or more, preferably 1 to 4, more preferably 1 to 2, groups selected from those recited herein as appropriate for the recited moiety. Thus, for example, an optionally-substituted alkylamino group refers to the group —NR'R", wherein R' and R" are selected from hydrogen, alkyl, substituted alkyl, alkenyl, substituted alkenyl, cycloalkyl, and substituted cycloalkyl, provided R' and R" are not both hydrogen, as in that case the group is amino and not optionally-substituted alkylamino.

A cycloamino group refers to a group —NR'R", wherein R' and R" join to form a monocyclic heterocyclo ring, such as, for example, N-morpholinyl, N-piperidinyl, N-piperazinyl and the like. A "substituted cycloamino" is a cycloamino group having one or more, preferably one to 4, more preferably one to 2, substituents selected from those recited below for substituted heterocyclo groups.

The term "alkylthio" refers to the group $SR_g$, wherein $R_g$ is selected from alkyl, alkenyl, and cycloalkyl. A $C_1$-$C_4$alkylthio is an alkylthio group $SR_{g'}$, wherein $R_{g'}$ is a $C_1$-$C_4$alkyl or $C_3$-$C_4$cycloalkyl. A substituted alkylthio group is an alkylthio group wherein at least one of the alkyl, alkenyl, and/or cycloalkyl moieties is substituted with one or more, preferably 1 to 4, more preferably 1 to 2, groups selected from those recited above for substituted alkenyl groups.

The term "aryl" refers to cyclic, aromatic hydrocarbon groups which have 1 to 3 aromatic rings, including phenyl and naphthyl. The aryl group may have fused thereto a second or third ring which is a heterocyclo, cycloalkyl, or heteroaryl ring, provided in that case the point of attachment will be to the aryl portion of the ring system. Thus, exemplary aryl groups include,

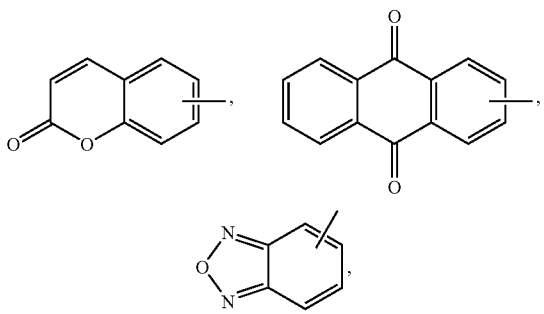

and so forth.

"Substituted aryl" refers to an aryl group substituted by one or more substituents, preferably 1 to 3 substituents, more preferably 1 to 2 substituents, at any point of attachment of the aryl ring and/or of any further ring fused thereto. Exemplary substituents include, but are not limited to, alkyl, substituted alkyl, and where valence allows those groups recited above as exemplary substituents for substituted alkyl groups.

The term "cycloalkyl" refers to a fully saturated and partially unsaturated cyclic hydrocarbon group containing from 1 to 3 rings and 3 to 8 carbons per ring. Exemplary such groups include cyclopropyl, cyclobutyl, cyclopentyl, cyclohexyl, cycloheptyl, cyclobutenyl, cyclopentenyl, cyclohexenyl, etc. A cycloalkyl ring may have a carbon ring atom replaced with a carbonyl group (C=O), as illustrated below. Cycloalkyl groups include such rings having a second or third ring fused thereto that is a heterocyclo, heteroaryl, or aryl group, provided that in such cases the point of attachment is to the cycloalkyl portion of the ring system. The term "cycloalkyl" also includes such rings having a second or third ring attached to the ring or ring system in a spiro fashion wherein the spiro ring is either a heterocyclo or carbocyclic ring. "Substituted cycloalkyl" refers to a cycloalkyl group as defined above having one or more substituents, preferably 1 to 4 substituents, more preferably 1 to 2 substituents, at any available point of attachment on either the cycloalkyl ring and where valence allows on any rings fused or attached thereto. Exemplary substituents include, but are not limited to, alkyl, substituted alkyl, and those groups recited above as exemplary substituents for substituted alkyl groups.

Thus, as an illustration non-limiting examples of cycloalkyl rings may include,

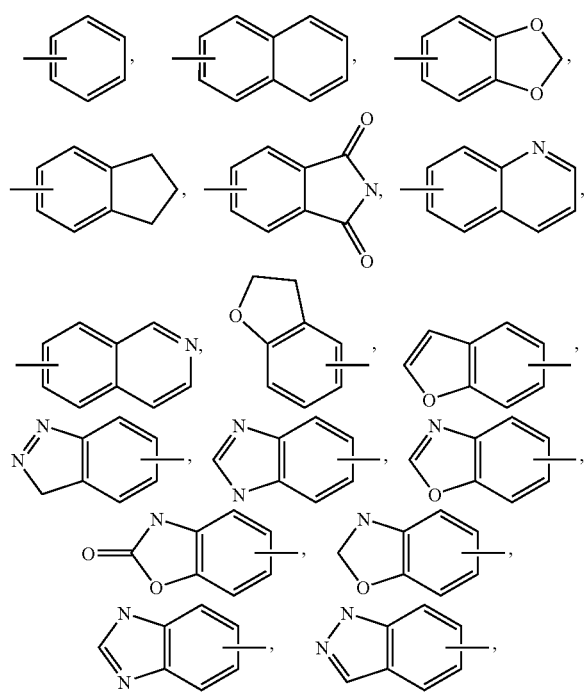

-continued

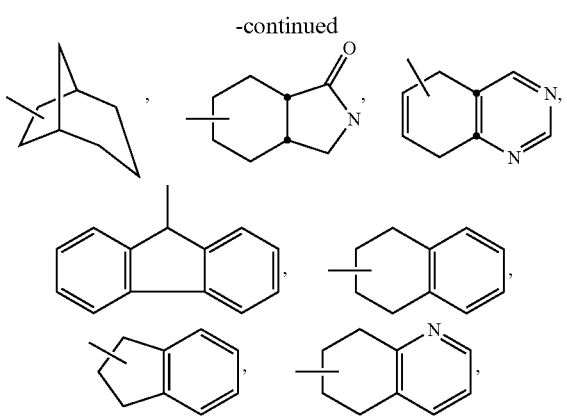

and the like.

The terms "heterocycle," "heterocyclic" and "heterocyclo" refer to fully saturated or partially unsaturated non-aromatic cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. A heterocyclo ring may have a carbon ring atom replaced with a carbonyl group (C=O), as illustrated above for cycloalkyl groups. The heterocyclic group may be attached to the remainder of the molecule at any nitrogen atom or carbon atom of the ring or ring system. Additionally, the heterocyclo group may have a second or third ring attached thereto in a spiro or fused fashion, provided the point of attachment is to the heterocyclo group. An attached spiro ring may be a carbocyclic or heterocyclic ring and the second and/or third fused ring may be a cycloalkyl, aryl or heteroaryl ring. Exemplary monocyclic heterocyclic groups include azetidinyl, pyrrolidinyl, pyrazolinyl, imidazolidinyl, oxazolidinyl, piperidinyl, piperazinyl, morpholinyl, tetrahyrdofuryl, tetrahydropyranyl, thiamorpholinyl, and the like.

Exemplary bicyclic heterocyclic groups include indolinyl, isoindolinyl, quinuclidinyl, benzopyrrolidinyl, benzopyrazolinyl, benzoimidazolidinyl, benzopiperidinyl, benzopiperazinyl, tetrahydroisoquinolinyl, tetrahydroquinolinyl, dihydroisoindolyl and the like.

"Substituted heterocycle," "substituted heterocyclic," and "substituted heterocyclo" refer to heterocycle, heterocyclic or heterocyclo groups substituted with one or more substituents, preferably 1 to 4 substituents, more preferably 1 to 2 substituents, at any available point of attachment to the heterocyclo ring and/or any ring fused or attached thereto in a spiro fashion. Exemplary substituents include, but are not limited to, alkyl, substituted alkyl, and those groups recited above as exemplary substituents for substituted alkyl groups.

The term "heteroaryl" refers to aromatic cyclic groups (for example, 5 to 6 membered monocyclic, 7 to 11 membered bicyclic, or 10 to 16 membered tricyclic ring systems) which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heteroaryl group may be attached to the remainder of the molecule at any nitrogen atom or carbon atom of the ring or ring system. Additionally, the heteroaryl group may have a second or third carbocyclic (cycloalkyl or aryl) or heterocyclic ring fused thereto provided the point of attachment is to the heteroaryl group.

Exemplary monocyclic heteroaryl groups include pyrazolyl, imidazolyl, triazolyl, oxazolyl, furyl, thiazolyl, isoxazolyl, thiazolyl, pyridyl

[i.e., 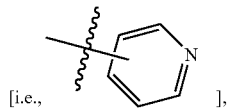 ], pyridazinyl

[i.e., 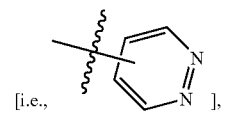 ], pyrimidinyl

[i.e., 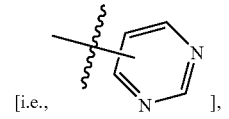 ], pyrazinyl

[i.e., 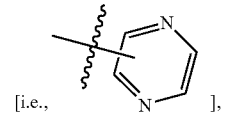 ], triazinyl, and the like. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), triazinylazepinyl, and the like.

"Substituted heteroaryl" refers to heteroaryl groups substituted with one or more substituents as valence allows, preferably 1 to 3 substituents, more preferably 1 to 2 substituents, at any available point of attachment to the heteroaryl ring and/or any ring fused thereto. Exemplary substituents include, but are not limited to, alkyl, substituted alkyl, and those groups recited above as exemplary substituents for substituted alkyl groups.

When reference is made to an optionally-substituted, specifically-named aryl, heteroaryl, cycloalkyl, or heterocyclo ring, the optional substituents may be selected as valence allows from the groups recited above for the genus of rings of which the specifically-named group is a member. For example, "optionally-substituted phenyl" includes unsubstituted phenyl rings as well as phenyl rings containing one or more substituents selected from those recited above for aryl groups. "Optionally-substituted pyridyl, pyridazinyl, pyrimidinyl, and pyrazinyl," includes unsubstituted pyridyl, pyridazinyl, pyrimidinyl, and pyrazinyl rings, as well as such rings containing one or more substituents selected from those recited above for heteroaryl groups.

The term "optionally substituted oxadiazolyl" as used herein is intended to refer to the group,

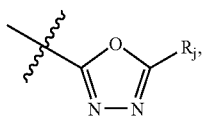

wherein $R_j$ is selected from a substituent recited above for substituted heteroaryl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine and/or iodine.

The term haloalkyl refers to an alkyl group having a single halo substituent or multiple halo substitutents forming, for example, groups such as a perfluoroalkyl group including trichloromethyl or trifluoromethyl ($CCl_3$ or $CF_3$). A halo$C_1$-$C_4$alkyl refers to a $C_1$-$C_4$alkyl having one or more halo substituents.

The term haloalkoxy refers to an alkoxy group as defined above wherein the alkyl moiety has a single halo substituent or multiple halo substitutents forming, for example, groups such as a trifluoromethoxy. A halo$C_1$-$C_4$alkoxy refers to a $C_1$-$C_4$alkoxy having one or more halo substituents.

The term "saturated" when used herein is intended to refer to fully saturated and partially saturated moieties, and conversely, "unsaturated" refers to fully unsaturated and partially unsaturated moieties.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

The term "selective" as used herein with reference to the capability of the claimed compounds to inhibit p38 activity means that the compound in question has a level of activity as measured in enzyme assays for inhibiting the p38α/β kinase that is significantly greater than the activity of the compound in inhibiting a plurality of other kinases falling within families throughout the human kinome. The term "significantly greater activity" includes the activity of at least one compound having about 500-fold or more greater activity for inhibiting p38α/β enzyme as compared with the activity of the compound in inhibiting other kinases, for example, as compared with the activity of the compound in inhibiting about twenty-five or more other kinases, in another example, as compared with about fifty or more other kinases, and in yet another example, as compared with about 100 or more other kinases. Thus, a selective p38 inhibitor as defined herein according to one embodiment will inhibit the α-isoform of the p38 kinase, the β-isoform of the p38 kinase, and/or both the α and β forms of the p38 kinase, at least 500 times greater than it will inhibit any one of a plurality of other kinases. Thus, for example, considering an embodiment involving comparison with a sample of twenty-five other kinases, p38 selective compounds will have 500 times greater activity in inhibiting p38α/β kinase as compared with any one of each of the twenty-five other kinases considered individually (e.g., in a one-on-one comparison). In another embodiment of the invention, compounds are provided having at least about 1,000-fold greater activity for inhibiting p38α/β kinase as compared with other kinases, for example, as compared with about twenty-five or more, about fifty or more, and in yet another example, as compared with about 100 or more other kinases. In yet another embodiment of the invention, compounds are provided having at least about 5,000-fold greater activity for inhibiting p38α/β kinase as compared with other kinases, for example, as compared with about twenty-five or more other kinases, as compared with about fifty or more other kinases, and in yet another example, as compared with about 100 or more other kinases. The term "highly selective" as used herein means the compound in question has at least about 10,000 fold greater activity for inhibiting the p38α/β kinase enzyme as compared with at least thirty other kinases, more preferably, as compared with at least about fifty or more other kinases. When reference is made herein to "other kinases", applicant intends to refer to kinases known in the field other than the p38α/β kinases. For example, various known kinases and kinase families other than the 38α/β kinase are identified in WO 02/062804, and in Manning, G. et al., "The Protein Kinase Complement of the Human Genome", *Science* (Washington, D.C., United States) (2002), 298(5600), at pp. 1912-1916, 1933-1934, which is incorporated herein by reference. "Other kinases" as identified therein thus may include, without limitation, one or more kinases chosen from the following kinases and/or kinase families: CaMK1, CaMK2, CDK, DAPK, EMT, FGF, FMS, GSK3, LCK, PDGF-R, PKA, PCK, RAF, RIPK, LIMK-1, SYK, Met, PAK-4, PAK-5, ZC-1, STLK-2, DDR-2, Aurora 1, Aurora 2, Bub-1, PLK, Chk1, Chk2, HER$_2$, JAK, raf1, MEK1, EGF-R, RSK/RSK, IGF-R, IRAK, VEGF-R, P13K, PDK, HIPK, STKR, BRD, Wnk, NKF3, NKF4, NKF5, weel kinase, Src, Ab1, ILK, MK-2, IKK-2, RIPK, Cdc7, Ste11, Ste20, Ste7, Tec, Trk, and/or Nek, and so forth. The above is an exemplary, non-limiting list of other kinases. Manning identified 518 protein kinases, and applicant intends to incorporate each one of these 518 protein kinases other than the p38 kinase in the definition of the term "other kinases" as used herein.

There are many enzyme assays known in the field that may be used to measure the levels of activity to determine selectivity. Applicant has described certain enzyme assays below but does not intend to be limited to use of these specific assays with regard to the definition of selectivity herein.

Unless otherwise indicated, a heteroatom with an unsatisfied valence is understood to have hydrogen atoms sufficient to satisfy the valences, as one skilled in the field will appreciate.

The compounds of formula I may form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts may also be useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

When reference is made herein to a compound of formula (I) herein, this is intended to refer to each compound of formula (I), and each salt, prodrug, solvate, or isomer thereof, alone or in combination with other compounds of formula (I), other salts, prodrugs, solvates, or isomers of compounds of formula (I), or other compounds not of formula (I), without limitation to the manner in which said compound of formula (I), or salt, prodrug, solvate, or isomer thereof is made or formed, for example, whether existing in a pure form, isolated form, crude form, together with one or more excipients or impurities, existing in a solid or liquid form, in a pharmaceutical preparation before administration to a patient, as formed in the body of a patient after administration to a patient, and so forth.

Throughout the specification, groups and substituents thereof may be chosen to provide stable moieties and compounds.

Alternate Embodiments

According to one aspect of the invention, compounds are providing having the formula,

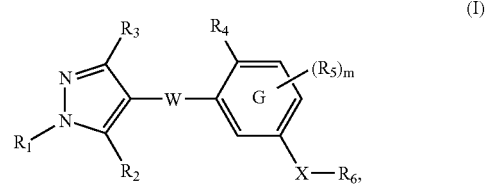

wherein:

ring G is phenyl or pyridyl;

W is —NH(C=O)—, —CH$_2$NH—, —NHCH$_2$—, —CH$_2$—O—, or —(C=O)O—;

R$_1$ is alkyl, substituted alkyl, aryl, substituted aryl, heteroaryl, or substituted heteroaryl;

R$_2$ is hydrogen, alkyl, substituted alkyl, alkoxy, substituted alkoxy, amino, alkylamino, substituted alkylamino, cycloamino, or substituted cycloamino;

R$_3$ is hydrogen or lower alkyl;
R$_4$ is hydrogen, C$_{1-4}$alkyl, or halogen;
R$_5$ is as defined previously in the summary of invention;
X is —(C═O)NH—, or is absent;
R$_6$ is hydrogen, alkyl or substituted alkyl, cycloalkyl or substituted cycloalkyl, heterocycle or substituted heterocycle, heteroaryl or substituted heteroaryl; or alternatively, R$_6$ is joined together with a group R$_5$ on an adjacent carbon atom to form an optionally-substituted, fused five to six membered heterocyclic or carbocyclic ring; and
m is 0, 1, or 2; or a pharmaceutically-acceptable salt, hydrate, solvent, isomer, or prodrug thereof.

According to another aspect of the invention, compounds are provided having the formula,

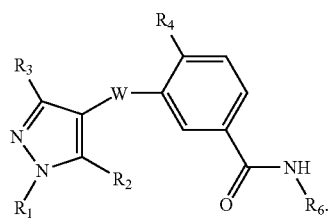

According to another aspect of the invention, compounds are provided wherein W is —NH(C═O)—.

According to another aspect of the invention, compounds are provided wherein W is —CH$_2$NH— or —NHCH$_2$—.

According to another aspect of the invention, compounds are provided wherein W is —CH$_2$—O—, or —(C═O)O—.

According to another aspect of the invention, compounds are provided having the formula,

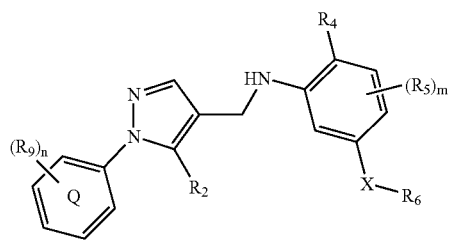

wherein R$_9$ is selected from alkyl or substituted alkyl, trifluoromethyl, trifluoromethoxy, halogen, cyano, nitro, OH, OR$_{10}$, SR$_{10}$, and S(═O)$_2$R$_{10}$, wherein R$_{10}$ is lower alkyl; and n is 0, 1, 2 or 3.

According to another aspect of the invention, compounds are provided wherein:
Q is phenyl or pyridyl;
R$_6$ is C$_1$-C$_4$ alkyl or substituted C$_1$-C$_4$ alkyl, cycloalkyl or substituted cycloalkyl;
R$_2$ is lower alkyl, amino, or alkylamino; and
R$_4$ is lower alkyl or halogen.

According to another aspect of the invention, compounds are provided wherein:
R$_1$ is C$_1$-C$_4$ alkyl or substituted C$_1$-C$_4$ alkyl, cycloalkyl or substituted cycloalkyl, heterocycle or substituted heterocycle, aryl or substituted aryl;
R$_6$ is cyclopropyl;
R$_2$ is hydrogen, trifluoromethyl, halogen, C$_1$-C$_4$ alkyl or substituted C$_1$-C$_4$ alkyl, NR$_7$R$_8$, or OR$_8$;

R$_3$ is hydrogen, C$_1$-C$_4$ alkyl or substituted C$_1$-C$_4$ alkyl;
R$_4$ is lower alkyl or halogen; and
m is 0-1.

According to another aspect of the invention, compounds are provided wherein R$_3$ is hydrogen and R$_4$ is methyl.

According to another aspect of the invention, compounds are provided wherein one of R$_5$ and R$_6$ form a heteroaryl so that ring Q is a group selected from:

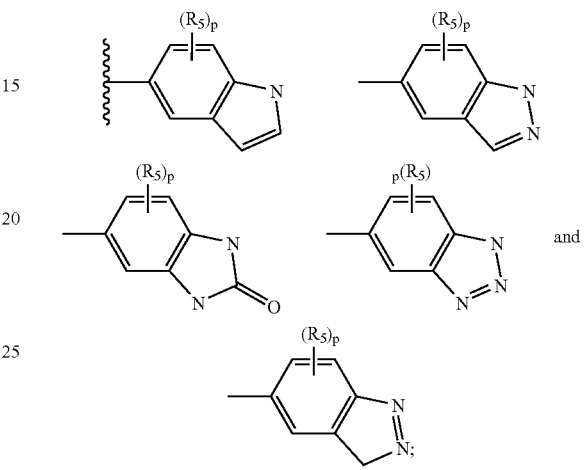

wherein p is 0, 1 or 2; and/or pharmaceutically-acceptable salts, prodrugs, solvates, isomers, and/or hydrates thereof.

According to another aspect of the invention, compounds are provided wherein R$_1$ is selected from:

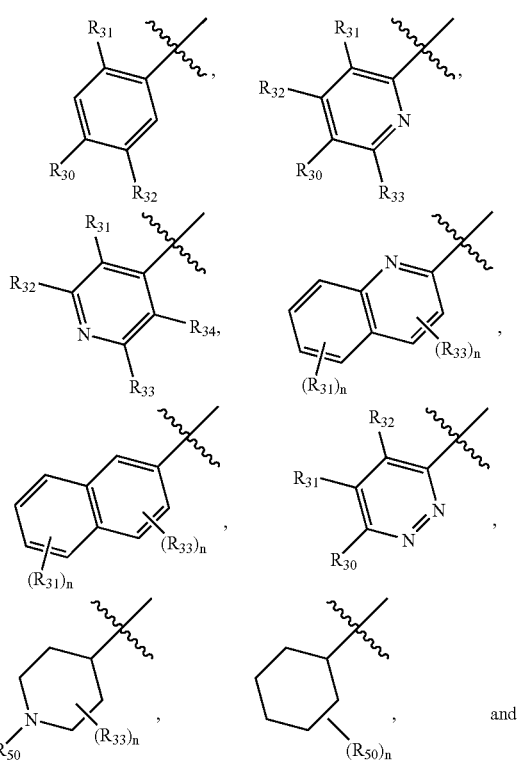

-continued

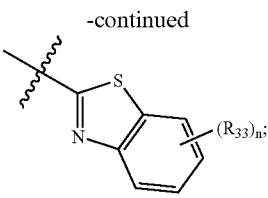

$R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, $O(C_{1-4}$alkyl), nitro, and/or $SO_2CH_3$; and $R_{50}$ is hydrogen, alkyl, or arylalkyl; and n is at each occurrence independently selected from 0-3; and/or pharmaceutically-acceptable salts, prodrugs, solvates, isomers, and/or hydrates thereof.

According to another aspect of the invention, compounds are provided wherein $R_1$ is optionally-substituted aryl or heteroaryl;

$R_2$ is hydrogen, lower alkyl, halogen, haloalkyl, trifluoromethyl, $NH_2$, NH(alkyl), NH(cycloalkyl), N(alkyl)$_2$, or —$CH_2$—O—$CH_3$, wherein each of said alkyl groups of NH(alkyl), and/or N(alkyl)$_2$, are in turn optionally substituted with one to two of OH, $O(C_{1-4}$alkyl), imidazolyl, pyridyl, phenyl, tetrahydrofuryl, $NH_2$, NH(alkyl), N(alkyl)$_2$, and/or N-morpholinyl;

$R_3$ is hydrogen or methyl;

$R_4$ is methyl or halogen;

X is —C(=O)NH— or is absent;

$R_6$ is lower alkyl or cyclopropyl, or when X is absent, $R_6$ is optionally-substituted heteroaryl; and m is 0 or 1; and/or pharmaceutically-acceptable salts, prodrugs, solvates, isomers, and/or hydrates thereof.

According to another aspect of the invention, compounds are provided wherein $R_6$ is selected from the group consisting of:

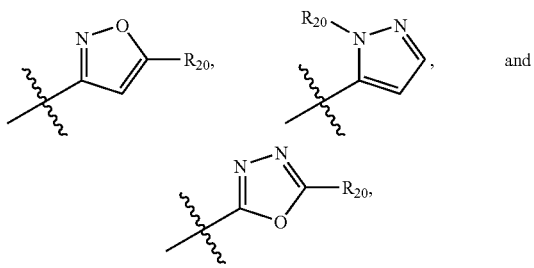

wherein $R_{20}$ is hydrogen, lower alkyl or phenyl.

According to another aspect of the invention, compounds are provided having the formula,

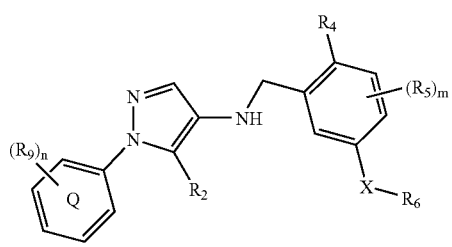

wherein, $R_2$ is hydrogen, lower alkyl, halogen, haloalkyl, trifluoromethyl, $NH_2$, NH(alkyl), NH(cycloalkyl), N(alkyl)$_2$, or —$CH_2$—O—$CH_3$, wherein each of said alkyl groups of NH(alkyl), and/or N(alkyl)$_2$, are in turn optionally substituted with one to two of OH, $O(C_{1-4}$alkyl), imidazolyl, pyridyl, phenyl, tetrahydrofuryl, $NH_2$, NH(alkyl), N(alkyl)$_2$, and/or N-morpholinyl;

$R_4$ is methyl or halogen;

X is —C(=O)NH— or is absent;

$R_6$ is lower alkyl or cyclopropyl, or when X is absent, $R_6$ is optionally-substituted heteroaryl;

$R_9$ is selected from alkyl or substituted alkyl, trifluoromethyl, trifluoromethoxy, halogen, cyano, nitro, OH, $OR_{10}$, $SR_{10}$, and $S(=O)_2R_{10}$, wherein $R_{10}$ is lower alkyl;

m is 0 or 1; and n is 0, 1, 2 or 3; and/or pharmaceutically-acceptable salts, prodrugs, solvates, isomers, and/or hydrates thereof.

Further aspects of the invention may be apparent to one skilled in the field upon reading the disclosure herein, e.g., considering the examples below.

Utility

The compounds of the invention are selective inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Graves' disease. The inventive compounds may be used to infectious diseases such as sepsis, septic shock, Shigellosis, and Heliobacter Pylori.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS, ARC or malignancy, and herpes.

The inventive compounds also may be used to treat angiogenic disorders including solid tumors, ocular neovasculization, and infantile haemangiomas.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating p38 kinase-associated conditions may comprise administering compounds of Formula (I) alone or in combination with each other and/or other suitable therapeutic agents such as anti-inflammatory drugs, antibiotics, anti-viral agents, antioxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR$_{1384}$), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 10/315,818, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as diltiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of within the scope of formula (I) may be tested for activity as inhibitors of p38α/β enzymes and TNF-α using the assays described below, or variations thereof that are within the level ordinary skill in the art. Compounds described in the examples herein have shown activity as inhibitors of p38α/β enzymes and TNF-α.

Biological Assays

Generation of p38 Kinases cDNAs of human $p^{38}\alpha$, β and γ isozymes are cloned by PCR. These cDNAs can be subcloned in the pGEX expression vector (Pharmacia). GST-p38 fusion protein is expressed in E. Coli and purified from bacterial pellets by affinity chromatography using glutathione agarose. p38 fusion protein is activated by incubating with constitutively active MKK6. Active p38 is separated from MKK6 by affinity chromatography. Constitutively active MKK6 is generated according to Raingeaud et al. [Mol. Cell. Biol., 1247-1255 (1996)].

TNF-α Production by LPS-Stimulated PBMCs

Heparinized human whole blood is obtained from healthy volunteers. Peripheral blood mononuclear cells (PBMCs) are purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension is incubated with 50 ul of test compound (4× concentration in assay medium containing 0.2% DMSO) in 96-well tissue culture plates for 5 minutes at RT. 100 ul of LPS (200 ng/ml stock) is then added to the cell suspension and the plate is incubated for 6 hours at 37° C. Following incubation, the culture medium is collected and stored at −20° C. TNF-α concentration in the medium is quantified using a standard ELISA kit (Pharmingen-San Diego, Calif.). Concentrations of TNF-α and $IC_{50}$ values for test compounds (concentration of compound that inhibited LPS-stimulated TNF-α production by 50%) are calculated by linear regression analysis.

p38 Assay

The assays are performed in V-bottomed 96-well plates. The final assay volume is 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 is pre-incubated with test compounds for 10 min. prior to initiation of reaction with substrates. The reaction is incubated at 25° C. for 45 min. and terminated by adding 5 µl of 0.5 M EDTA to each sample. The reaction mixture is aspirated onto a pre-wet filtermat using a Skatron Micro96 Cell Harvester (Skatron, Inc.), then washed with PBS. The filtermat is then dried in a microwave oven for 1 min., treated with MeltilLex A scintillation wax (Wallac), and counted on a Microbeta scintillation counter Model 1450 (Wallac). Inhibition data are analyzed by nonlinear least-squares regression using Prizm (GraphPadSoftware). The final concentration of reagents in the assays are ATP, 1 µM; [γ-$^{33}$P]ATP, 3 nM,; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) are injected intraperitoneally with 50 ug/kg lipopolysaccharide (LPS; E coli strain 0111:B4, Sigma) suspended in sterile saline. Ninety minutes later, mice are sedated by $CO_2:O_2$ inhalation and a blood sample was obtained. Serum is separated and analyzed for TNF-alpha concentrations by commercial ELISA assay per the manufacturer's instructions (R&D Systems, Minneapolis, Minn.).

Test compounds are administered orally at various times before LPS injection. The compounds are dosed either as suspensions or as solutions in various vehicles or solubilizing agents.

Abbreviations

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P or iPr=isopropyl
MeOH=methanol
EtOH=ethanol
EtOAc=ethyl acetate
Boc=tert-butyloxycarbonyl
DCM=dichloromethane
DCE=1,2-dichloroethane
DMF=N,N-dimethyl formamide
DMF-DMA=N,N-dimethyl formamide dimethyl acetal
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
BOP=benzotriazol-1-yloxy-tris(dimethylamino)-phosphonium hexafluorophosphate
DPPA=diphenylphosphoryl azide
KOH=potassium hydroxide
$K_2CO_3$=potassium carbonate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
Pd=palladium
Pd/C=palladium on carbon
min=minute(s)
h or hr=hour(s)
L=liter
mL=milliliter
µL=microliter
g=gram(s)
mg=milligram(s)
mol=moles mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
Prep HPLC=preparative reverse phase HPLC
LC/MS=high performance liquid chromatography/mass spectrometry
MS=mass spectrometry
NMR=nuclear magnetic resonance
mp=melting point HPLC Conditions: YMC S5 ODS 4.6×50 mm Ballistic column, 4 mL/min flow rate, 4 min. linear gradient elution (Start solvent % B=0; Final solvent % B=100), solvent A=10% MeOH/90% $H_2O$/0.2% $H_3PO_4$. Solvent B=90% MeOH/10% $H_2O$/0.2% $H_3PO_4$.

The above HPLC condition is used throughout the specification except where the superscript a is used, in which case the following conditions are used: Column: Phenomenex 4.6×30 mm; Flow rate: 5 mL/min; Gradient time: 2 min with 1 min hold; Detection wave length: 220 nm; Starting solvent: 10% MeOH-90% H2O-0.1% TFA; and Final solvent: 90% MeOH-10% H2O-0.1% TFA.

Microwave Chemistry: Microwave reactions were performed using the commercially available Smith Synthesizer from Personal Chemistry. This reactor allows for precise control over reaction temperatures and times and greater than atmospheric pressures.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

EXAMPLE 1

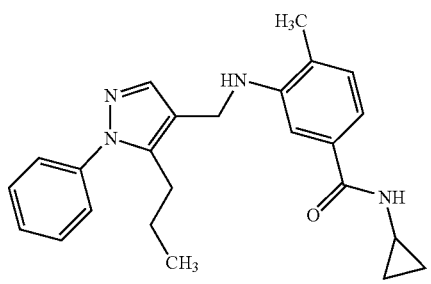

Step A:

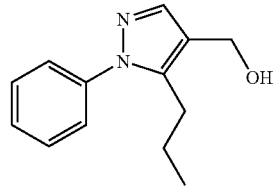

(1A)

To a solution of 1-phenyl-5-propyl-1H-pyrazole-4-carbonyl chloride (245 mg, 0.99 mmol) in THF (4 mL), at −78° C. was added LAH (1 M, 3 mL, 3.0 mmol). The reaction was stirred for 1 hr at −78° C., then sat. aq. $NH_4Cl$ and water were added and the product was extracted with EtOAc to afford (1A) as a yellow gel (228 mg).

Step B:

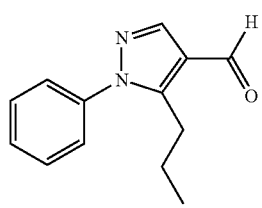

(1B)

A mixture of (1A) (700 mg, 3.2 mmol) and $MnO_4$ (1.36 g, 194.4 mmol) in THF (10 ml) was stirred at RT overnight. The solution was filtered and concentrated to afford (1B) as a yellow gel (598 mg).

Step C:

To a solution of (1B) (83 mg, 0.20 mmol) and 3-amino-N-cyclopropyl-4-methyl-benzamide hydrochloride (45 mg, 0.20 mmol) in DCM (2 mL) at RT was added TFA (0.5 mL). After stirring for 30 min., $Et_3SiH$ (0.5 mL) was added and stirring continued for 2 hr. The reaction was quenched with sat. aq. $NaHCO_3$, stirring for 10 min, then extracted with EtOAc, and concentrated to afford Example 1 as a white solid after re-crystallization from DCM (0.032 g, 41%). HPLC ret. t. (min): 3.05, MW: 388.5, LCMS$[M+H]^+$=389.1.

EXAMPLES 2 TO 16

The following examples shown in Table 1 were prepared in a manner analogous to Example 1. In one or more examples herein, aldehyde intermetiate (1B) can be reacted with methyl magnesium bromide followed by oxidation with $MnO_2$ to afford a ketone, which subsequently may undergo reductive amination as described in Example 1 to give the compound of Formula (I).

TABLE 1

| Ex. No. | Structure | HPLC time (min.) | MS (M+) |
| --- | --- | --- | --- |
| 2 | 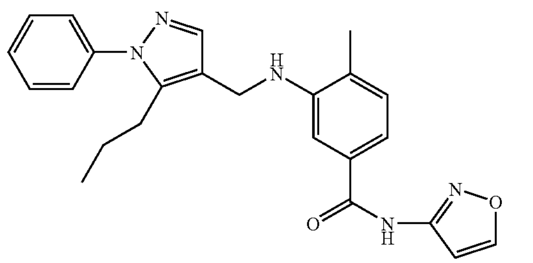 | 3.30 | 416.1 |
| 3 | 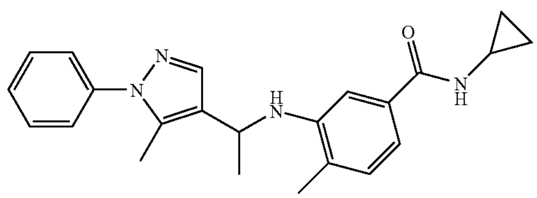 | 2.30 | 375.1 |
| 4 | 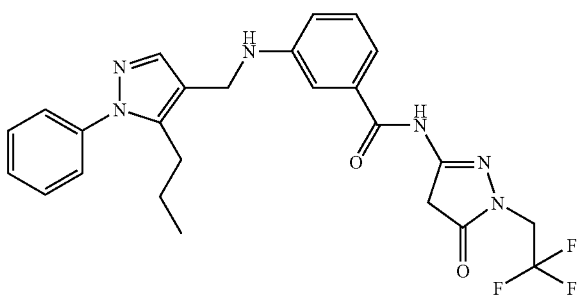 | 3.33 | 499.2 |
| 5 | 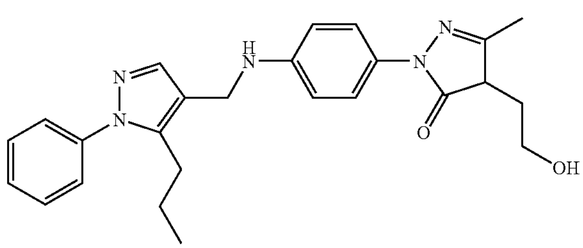 | 2.60 | 432.2 |
| 6 | 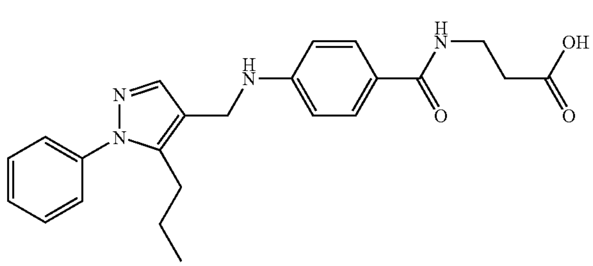 | 2.94 | 407.2 |

TABLE 1-continued

| Ex. No. | Structure | HPLC time (min.) | MS (M+) |
|---|---|---|---|
| 7 | 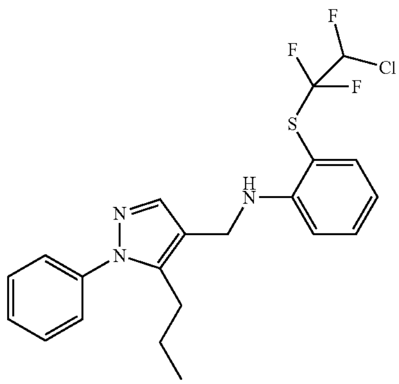 | 4.08 | 440.1 |
| 8 | 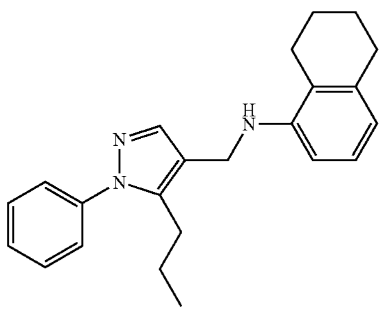 | 3.30 | 346.2 |
| 9 | 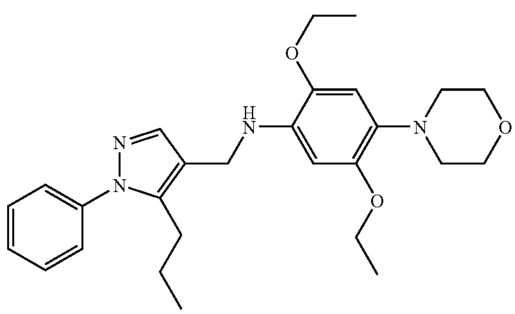 | 2.79 | 465.3 |
| 10 | 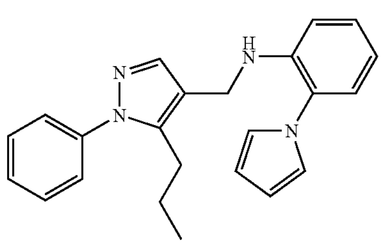 | 3.79 | 357.2 |
| 11 | 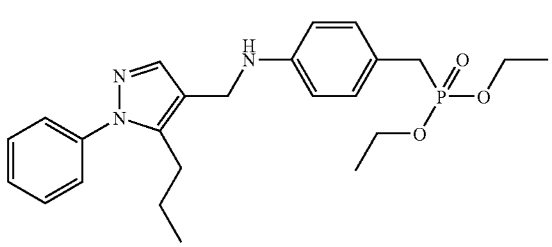 | 2.84 | 442.2 |

TABLE 1-continued

| Ex. No. | Structure | HPLC time (min.) | MS (M+) |
|---|---|---|---|
| 12 | 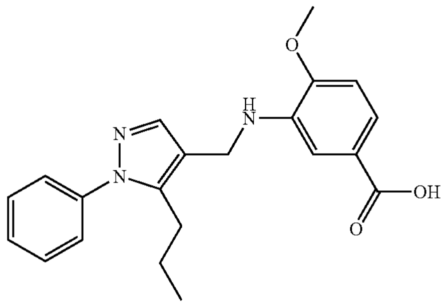 | 2.88 | 366.2 |
| 13 | 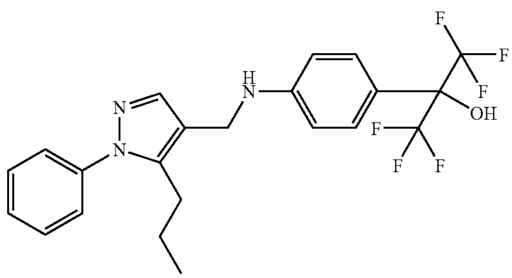 | 3.67 | 458.2 |
| 14 | 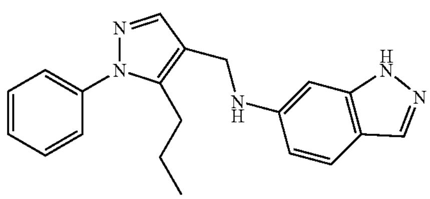 | 2.58 | 332.1 |
| 15 | 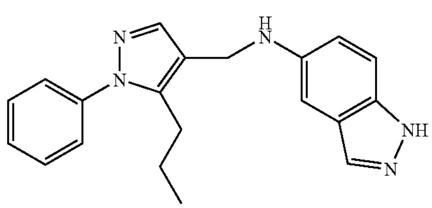 | 2.09 | 332.1 |
| 16 | 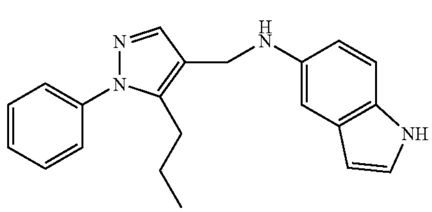 | 2.53 | 331.1 |

EXAMPLE 17

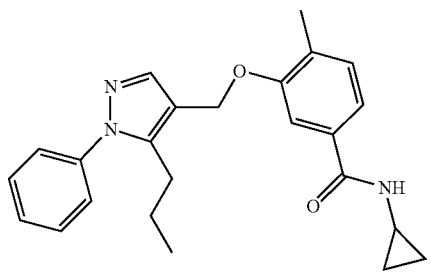

Step A:

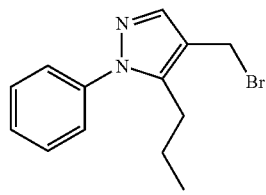
(17A)

To a solution of (1-phenyl-5-propyl-1H-pyrazol-4-yl)-methanol (1A) (244 mg, 1.13 mmol) in DCM (8 mL) was added POBr₃ (323 mg, 1.13 mmol) and the reaction was stirred at RT overnight. The solution was concentrated to afford (17A) (0.300 g), which was used in the next step without further purification.

Step B:

A solution of (17A) (0.050 g, 0.18 mmol) and DIPEA (0.100 mL) in THF (2 mL) was stirred for 15 min., then N-cyclopropyl-3-hydroxy-4-methyl-benzamide (0.020 g, 0.10 mmol), additional DIPEA (0.20 mL), and K₂CO₃ (0.32 g, 2.3 mmol) was added and stirring continued for 4 hr. NaH (60%, 0.008 g, 0.2 mmol) was added and the reaction was stirred for 2 hr. Water and sat. aq. NaHCO₃ were added and the product extracted with EtOAC. Purification by Prep HPLC afforded (17) as a yellow gel (0.0031 g). HPLC ret. t. (min): 3.85, MW: 389.5, LCMS[M+H]⁺=390.2.

EXAMPLE 18

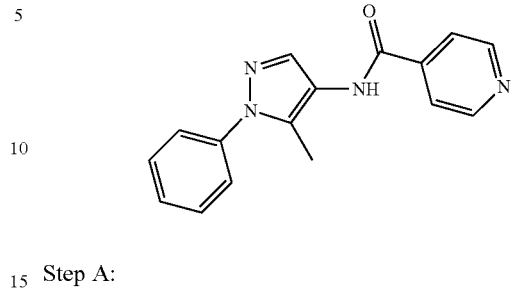

Step A:

(18A)

To a solution of 5-methyl-1-phenyl-1H-pyrazole-4-carboxylic acid (0.87 g, 4.63 mmol) in toluene (20 mL) was added Et₃N (1.7 mL, 11.6 mmol) and DPPA (2.54 mL, 11.6 mmol). The reaction was heated to 50° C. for 24 hr, tert-butyl alcohol (1.47 mL, 13.9 mmol) was added and stirring continued at 80° C. overnight. Water was added, and the reaction was cooled to RT over 1 hr. The intermediate carbamate was extracted with EtOAc. After concentration of the organics, a yellow gel (3 g) was obtained, which was used without further purification. The carbamate intermediate was dissolved in THF (10 mL) and HCl/Et₂O (10 mL) was added. After stirring for 2 hr at 35° C. the solvents were evaporated. DCM was added to the crude residue with vigorous stirring and the resulting precipitate was collected by filtration to afford (18A) as a white solid (268 mg).

Step B:

To a solution of pyrazole (18A) (0.025 g, 0.14 mmol) in DCM (2 mL) was added isonicotinoyl chloride hydrochloride (0.025 g, 0.14 mmol) and DIPEA (0.054 mL, 0.38 mmol). After stirring at RT overnight, the reaction was quenched with water and extracted with EtOAc. The organic extracts were washed with brine, dried over MgSO₄, filtered, and concentrated to afford (18) as a yellow solid (0.028 g). HPLC ret. t. (min): 1.75, MW: 278.3, LCMS[M+H]⁺=279.2.

EXAMPLES 19 TO 43

The following examples shown in Table 2 were prepared in a manner analogous to Example 18.

TABLE 2

| Ex. No. | Structure | HPLC time (min.) | MS (M⁺) |
|---|---|---|---|
| 19 | 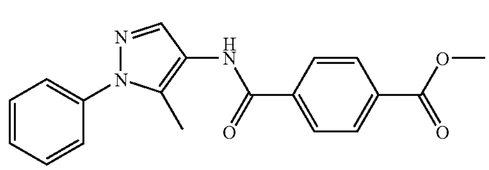 | 2.89 | 336.2 |

TABLE 2-continued

| Ex. No. | Structure | HPLC time (min.) | MS (M+) |
|---|---|---|---|
| 20 | 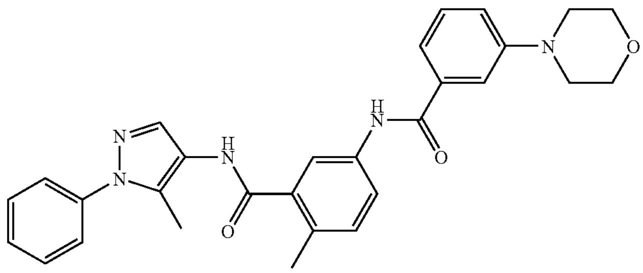 | 3.10 | 496.2 |
| 21 | 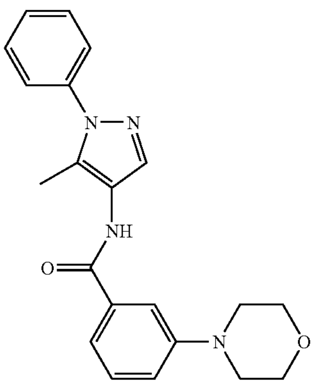 | 2.72 | 363.2 |
| 22 | 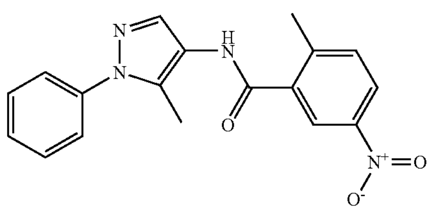 | 2.80 | 337.2 |
| 23 | 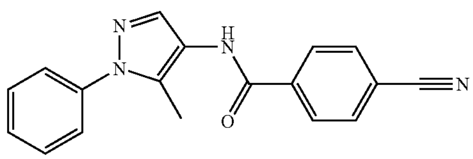 | 2.68 | 303.1 |
| 24 | 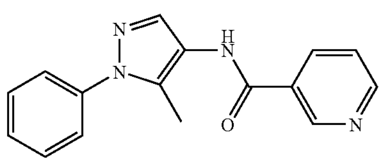 | 1.85 | 279.1 |
| 25 | 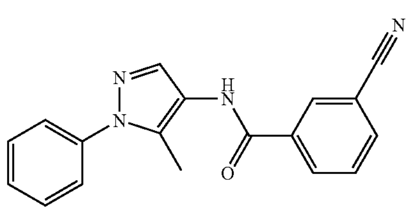 | 2.66 | 303.2 |
| 26 | 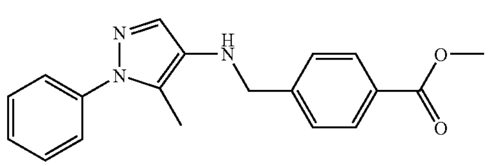 | 2.04 | 322.1 |

TABLE 2-continued

| Ex. No. | Structure | HPLC time (min.) | MS (M+) |
|---|---|---|---|
| 27 | 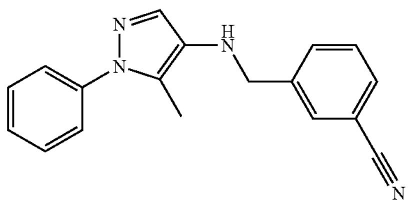 | 1.80 | 289.2 |
| 28 | 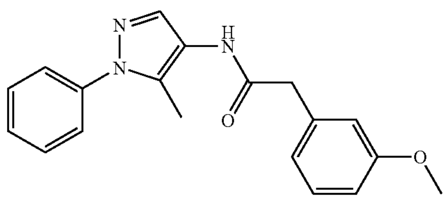 | 2.57 | 322.1 |
| 29 | 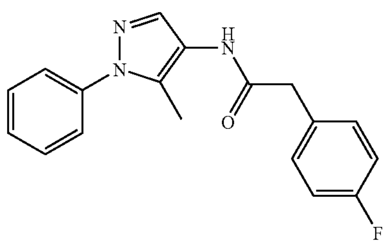 | 2.63 | 310.1 |
| 30 | 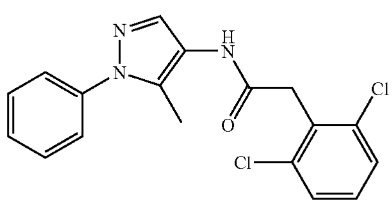 | 2.87 | 360.0 |
| 31 | 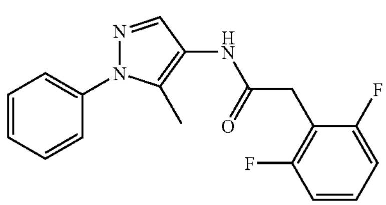 | 2.57 | 328.1 |
| 32 | 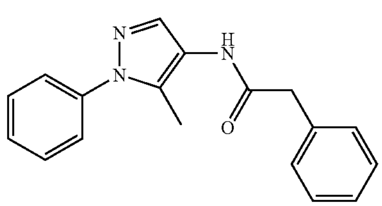 | 2.54 | 292.1 |
| 33 | 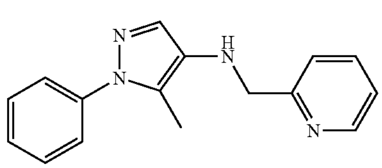 | 1.24 | 265.2 |

TABLE 2-continued

| Ex. No. | Structure | HPLC time (min.) | MS (M+) |
|---|---|---|---|
| 34 | 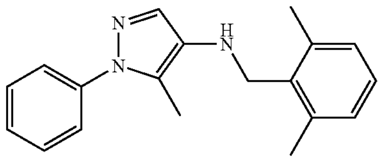 | 2.46 | 292.1 |
| 35 | 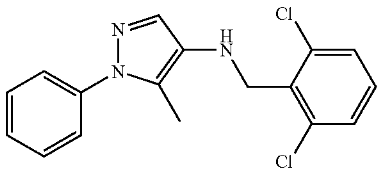 | 2.95 | 332.0 |
| 36 | 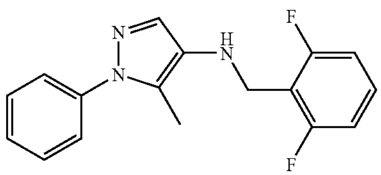 | 2.24 | 300.1 |
| 37 | 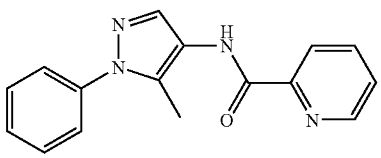 | 2.74 | 279.2 |
| 38 | 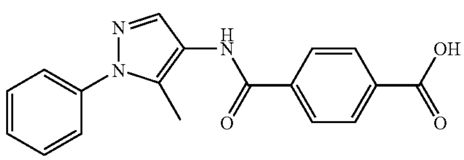 | 2.62 | 322.2 |
| 39 | 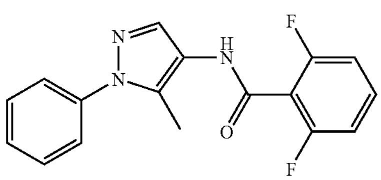 | 2.60 | 314.2 |
| 40 | 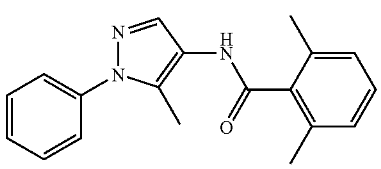 | 2.81 | 306.2 |
| 41 | 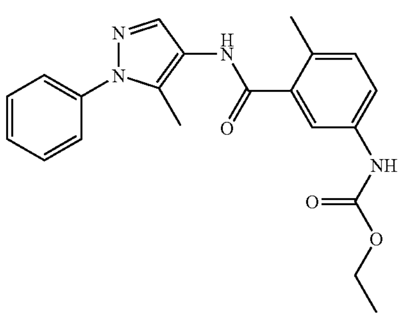 | 2.88 | 379.2 |

TABLE 2-continued

| Ex. No. | Structure | HPLC time (min.) | MS (M+) |
|---|---|---|---|
| 42 | 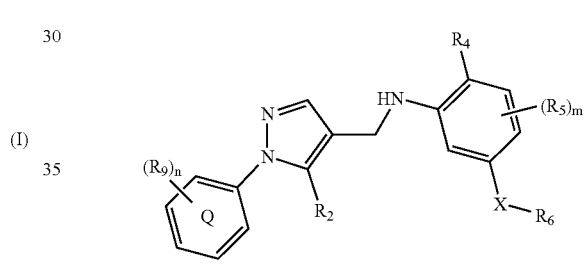 | 3.23 | 404.1 |
| 43 | 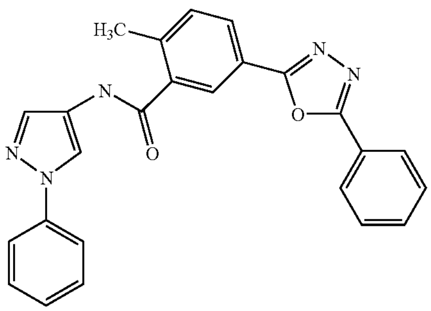 | | 421.46 |

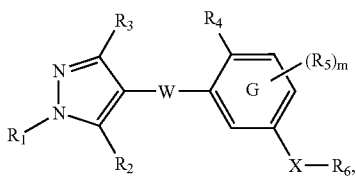

We claim:

1. A compound having the formula (I), (I)

wherein:

ring G is phenyl;
W is —CH(R$_8$)NH—, wherein R$_8$ is hydrogen or alkyl;
R$_1$ is hydrogen, alkyl, substituted alkyl, aryl, substituted aryl, heteroaryl, substituted heteroaryl, cycloalkyl, substituted cycloalkyl, heterocyclo or substituted heterocyclo;
R$_2$ is hydrogen, alkyl, or substituted alkyl;
R$_3$ is hydrogen, C$_{1-4}$alkyl, or substituted C$_{1-4}$alkyl;
R$_4$ is hydrogen, C$_{1-4}$alkyl, or substituted C$_{1-4}$alkyl;
X is —(C=O)NH—;
R$_6$ is hydrogen, alkyl or substituted alkyl, alkoxy or substituted alkoxy, phenoxy or substituted phenoxy, cycloalkyl or substituted cycloalkyl, heterocycle or substituted heterocycle, aryl or substituted aryl; and
m is 0; or a pharmaceutically-acceptable salt, hydrate, solvent, stereoisomer, or prodrug thereof.

2. A compound according to claim 1, having the formula, or a pharmaceutically acceptable salt or solvate thereof, wherein ring Q is phenyl, R$_9$ is selected from alkyl or substituted alkyl, trifluoromethyl, trifluoromethoxy, halogen, cyano, nitro, OH, OR$_{10}$, SR$_{10}$, and S(=O)$_2$R$_{10}$, wherein R$_{10}$ is lower alkyl; and n is 0, 1, 2 or 3.

3. The compound of claim 2, wherein:
Q is phenyl;
R$_6$ is C$_1$-C$_4$ alkyl or substituted C$_1$-C$_4$ alkyl, cycloalkyl or substituted cycloalkyl;
R$_2$ is lower alkyl or alkylamino; and
R$_4$ is lower alkyl.

4. The compound of claim 1, wherein:
R$_1$ is C$_1$-C$_4$ alkyl or substituted C$_1$-C$_4$ alkyl, cycloalkyl or substituted cycloalkyl, heterocycle or substituted heterocycle, aryl or substituted aryl;
R$_6$ is cyclopropyl;
R$_2$ is hydrogen, trifluoromethyl, C$_1$-C$_4$ alkyl or substituted C$_1$-C$_4$ alkyl; and
R$_4$ is lower alkyl.

5. The compound of claim 4, wherein R$_3$ is hydrogen and R$_4$ is methyl.

6. The compound of claim 1, wherein R$_3$ is hydrogen and R$_4$ is methyl.

7. A compound according to claim 1, wherein R$_1$ is selected from:

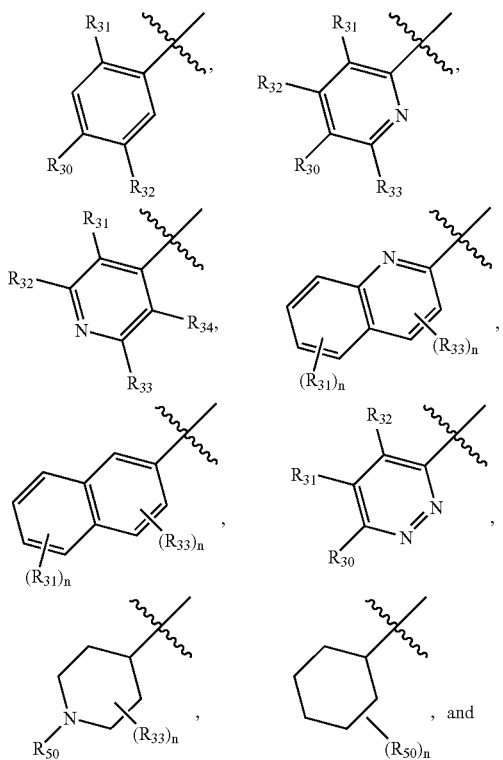

wherein
R$_{30}$, R$_{31}$, R$_{32}$, R$_{33}$ and R$_{34}$ are selected from hydrogen, halogen, cyano, trifluoromethyl, trifluoromethoxy, C$_{1-4}$alkyl, O(C$_{1-4}$alkyl), nitro, and/or SO$_2$CH$_3$; and
R$_{50}$ is hydrogen, alkyl, or arylalkyl; and n is at each occurrence independently selected from 0-3; and/or pharmaceutically-acceptable salts, prodrugs, solvates, isomers, and/or hydrates thereof.

8. A compound according to claim 1, wherein
R$_1$ is optionally-substituted aryl or heteroaryl;
R$_2$ is hydrogen, lower alkyl, haloalkyl, or trifluoromethyl;
R$_3$ is hydrogen or methyl;
R$_4$ is methyl;
R$_6$ is lower alkyl or cyclopropyl;
and/or pharmaceutically-acceptable salts, prodrugs, solvates, stereoisomer, and/or hydrates thereof.

9. The compound of claim 8, wherein R$_3$ is hydrogen.

10. A pharmaceutical composition comprising at least one compound according to claim 1 and a pharmaceutically-acceptable carrier or diluent.

* * * * *

UNITED STATES PATENT AND TRADEMARK OFFICE
CERTIFICATE OF CORRECTION

| | | |
|---|---|---|
| PATENT NO. | : 7,253,170 B2 | |
| APPLICATION NO. | : 11/477010 | |
| DATED | : August 7, 2007 | |
| INVENTOR(S) | : Alaric J. Dyckman et al. | |

It is certified that error appears in the above-identified patent and that said Letters Patent is hereby corrected as shown below:

In the Claims:

Claim 1 Column 41 Line 67 replace "solvent" with --solvate--

Claim 8 Column 44 Line 26 "stereoisomer" should be --stereoisomers--

Signed and Sealed this

Twentieth Day of May, 2008

JON W. DUDAS
*Director of the United States Patent and Trademark Office*